United States Patent [19]

Schäfer et al.

[11] Patent Number: 4,820,644
[45] Date of Patent: Apr. 11, 1989

[54] PROCESS FOR THE PREPARATION OF AN IMMUNE-REACTIVE POROUS CARRIER MATERIAL

[75] Inventors: Rainer Schäfer, Seehaupt; Helmut Jering, Tutzing, both of Fed. Rep. of Germany

[73] Assignee: Boehringer Mannheim GmbH, Mannheim-Waldhof, Fed. Rep. of Germany

[21] Appl. No.: 807,454

[22] Filed: Dec. 10, 1985

[30] Foreign Application Priority Data

Dec. 20, 1984 [DE] Fed. Rep. of Germany ....... 3446636

[51] Int. Cl.⁴ ................. G01N 33/543; G01N 33/537; G01N 33/539
[52] U.S. Cl. ..................................... 436/518; 436/512; 436/538; 436/539; 436/824; 436/826; 422/55; 422/56; 422/68; 422/69; 422/101
[58] Field of Search ............... 436/507, 506, 512, 518, 436/520, 509, 824, 539, 538, 826, 541; 422/55, 56, 68, 69, 101

[56] References Cited

U.S. PATENT DOCUMENTS

| 3,888,629 | 6/1975 | Bagshawe | 436/804 X |
|---|---|---|---|
| 3,966,897 | 6/1976 | Renn et al. | 436/515 |
| 4,205,954 | 6/1980 | Babson | 436/517 |
| 4,256,693 | 3/1981 | Kondo et al. | 422/56 |
| 4,310,504 | 1/1982 | Derfler et al. | 436/826 X |
| 4,495,296 | 1/1985 | Neurath et al. | 436/543 X |
| 4,619,896 | 10/1986 | Shatlck et al. | 436/826 X |
| 4,687,734 | 8/1987 | Chester | 436/824 X |

FOREIGN PATENT DOCUMENTS

| 0066648 | 12/1982 | European Pat. Off. . |
| 0008245 | 6/1979 | Fed. Rep. of Germany . |
| 0013156 | 12/1979 | Fed. Rep. of Germany . |
| 2523311 | 9/1983 | France ................................. 436/540 |
| 2065302 | 11/1980 | United Kingdom . |

OTHER PUBLICATIONS

S. N. Timasheff, G. D. Fasman, "Structure and Stability of Biological Macromolecules", 1969.

Primary Examiner—Robert J. Warden
Assistant Examiner—Jack Spiegel
Attorney, Agent, or Firm—Felfe & Lynch

[57] ABSTRACT

The present invention provides a process for the preparation of an immuno-reactive, porous carrier material by application of a solution of a first reaction component of an immuno-reaction and of a solution of a second component of an immuno-reaction coprecipitating therewith, incubation of the carrier material impregnated with the solutions for the immuno-precipitation, optional washing and subsequent drying of the impregnated carrier material, wherein a solution of both components of the immuno-reaction is prepared, which solution contains an inhibitor for the immuno-precipitation, the carrier material is impregnated with this solution and then the immuno-precipitation is initiated by removal of the inhibitor or by removal of the inhibiting action.

17 Claims, 7 Drawing Sheets

PROCESS FOR THE PREPARATION OF AN IMMUNE-REACTIVE POROUS CARRIER MATERIAL

The present invention is concerned with a process for the production of an immuno-reactive porous carrier material.

Immuno-reactive porous carrier materials play an important part in various branches of technology. For example, such materials are required for analytical and preparative processes in which one component of an immune reaction is used fixed to an insoluble matrix. The fixing of the component of the immune reaction to the insoluble carrier can take place by chemical or physical forces. Thus, methods for the production of covalent bonds between a solid carrier material and a chemical substance to be bound thereon have been known for a long time.

In general, however, a disadvantage of these methods is the fact that they bring about a chemical change of the biologically-active material which, in many cases, also results in a change of the biological activity.

Another known process is the inclusion polymerisation of such biologically-active substances. Here, as a rule, the molecule as such remains unchanged and, therefore, also retains its biological effectiveness unchanged. However, its accessibility to the other component of the immune reaction present in a liquid phase is drastically limited.

Therefore, in many cases, use has been made of a third known process which avoids the disadvantages of covalent binding and of inclusion polymerisation, namely, the adsorptive fixing to an appropriate carrier material. However, the method has, in turn, the disadvantage that binding to the solid carrier is substantially weaker than in the case of the two first-mentioned methods and, as a rule, an acceptable binding stability could only be achieved on particular synthetic resin surfaces.

Special problems arose with regard to the adhesive strength in the case of an adsorptive binding, i.e. when not only a covalent fixing but also an inclusion polymerisation is to be avoided, when porous carrier materials are employed.

From U.S. Pat. No. 3,888,629, a method is known which solves this problem of fixing adhesion by allowing a reaction to take place between the two components of an immune-reaction, i.e. between antibody and antigen, in the porous carrier material. For this purpose, the porous carrier material is impregnated either with a solution of the first component of the immuno-reaction and thereafter with a solution of the second component of the immune reaction, so that the immuno-reaction itself can take place in the porous carrier material with permanent fixing of the desired immuno-reactive material without chemical change or the disadvantages regarding its accessibility for other reaction components (see PCT-WO 82/02601), or, in a second known method, the two solutions of the particular components of the immune reaction are first rapidly mixed together and then the porous material is immediately impregnated therewith (see U.S. Pat. No. 3,888,629).

This method of binding an immune-reactive material on to a porous carrier material admittedly solves the abovedescribed problems but, nevertheless, displays another disadvantage, namely, a non-uniform distribution of the fixed immuno-reactive substance on the carrier material. This disadvantage is especially serious when this immuno-reactive porous carrier material is to be used, for example, for the purpose of the quantitative analysis of haptens or proteins in low concentrations. The requirement for stability of the antigen-antibody meshwork, as well as for low equilibrium-dissociation concentrations of the immuno-reactive component from the immuno-complexes relative to the concentration of the haptens or proteins to be determined, can only be achieved when the antibody used has a high affinity for the antigen in question. As is known from experience, the precipitate formation in the case of mixing such immuno-reactive components takes place spontaneously. In the case of the production of technical amounts of an immuno-adsorber by impregnation of a porous carrier material with solutions of the immuno-reactive components which have been mixed together shortly before, as is to be expected, a chronologically and spatially uncontrollable precipitate formation occurs on the carrier material.

The quantitative dosaging of the immunosorbent preferably takes place by cutting out a particular area of paper in the case of an immuno-reactive paper, by counting out a particular number of spheroids in the case of a spheroidal porous carrier material or by weighing out a definite amount of the immuno-reactive material. However, in the case of non-uniform distribution of the fixed immuno-reactive material, such simple methods of dosaging cannot be employed.

A further disadvantage of the known immune precipitation techniques is that very highly purified antigens are needed which requires a pre-purification by immunosorption, and is thus a laborious method of production.

Therefore, it is an object of the present invention to provide a simple method for the production of a porous immuno-reactive carrier material which has a superior homogeneity with regard to the distribution of the immune-reactive component and which can be produced easily and simply and which, in particular, does not require any laborious pre-purification for the production.

Thus, according to the present invention, there is provided a process for the production of an immuno-reactive porous carrier material by application of a solution of a first component of an immuno-reaction and of a solution of a second component of an immuno-reaction coprecipitating therewith, incubation of the carrier material impregnated with these solutions for immuno-precipitation, optional washing and subsequent drying of the impregnated carrier material, wherein a solution of both components of the immuno-reaction is prepared, which solution contains an inhibitor for the immune precipitation, the carrier material is impregnated with this solution and then the immuno-precipitation is initiated by removal of the inhibitor or by removal of the inhibiting action.

An important feature of the present invention is the use of an immuno-precipitation inhibitor which is reversibly active and which loses its inhibiting action by simple removal or by chemical change. In the presence of the inhibitor, the components of the immuno-reaction leading to the precipitation can be completely homogeneously distributed and, because of precipitation which only takes place very slowly, there is obtained a completely uniform covering of the carrier material with the particularly desired immuno-reactive substance which, even in the case of a large-scale batch, gives completely uniform and reproducible results.

In contradistinction to the known process of sequential application of antigen and antibody (heterogenous process), such as is described hereinafter in comparative Example 4, in the case of the "homogeneous" process according to the present invention, impregnation is carried out with a homogeneous solution of antigen and antibody. A differentiation is thereby to be made between two possible embodiments of the process according to the present invention: in the case of a "1 step process", the inhibitor which is contained in the impregnation solution is removed from the solution or is made inactive during the production process and, in the case of the "2-step process", the porous carrier is first pre-impregnated with an active material which removes the action of the inhibitor in the case of the subsequent impregnation with the immuno-reactive components.

One possibility for the removal of the inhibitor is a washing step before the drying and also, by means of additives to the wash solution, the action of the inhibitor in the porous carrier material can be removed.

However, the washing step is not an essential step of the process. Thus, for example, the precipitation can be initiated by evaporation of a volatile inhibitor.

As inhibitors of the immuno-precipitation, within the scope of the present invention there are preferably used those substances which are used as desorption agents in the case of immunosorptive purifications. For this purpose, there are especially preferred acids, bases and chaotropic ions of the Hofmeister series (lyotropic series) such as are described, for example, in "Structure and Stability of Biological Macromolecules", 1969, pub. Marcel Dekker Inc., New York, page 427, as well as certain organic compounds or solvents, such as acetonitrile, urea or glycerol.

As appropriate acids which can be used in the scope of the present invention, there can be employed not only volatile but also non-volatile acids. After impregnation of the carrier material, volatile acids can easily be removed for the removal of the inhibiting action, for example by heating, the application of a vacuum or the like. In the case of non-volatile acids, an analogous effect can be achieved by the addition of a salt of a volatile acid which is decomposed by the non-volatile acid, with the liberation of the volatile acid. Preferred examples include acetic acid, propionic acid and hydrochloric acid for the volatile acids. In the same way, volatile and non-volatile bases, for example ammonia and t-phosphate, can be used.

Furthermore, as inhibitors, there can also be used organic compounds which can reversibly influence not only the protein but also the water structure and which are described, for example, in J. F. Brandts "Conformational Transitions of Proteins in Water" contained in "Structure and Stability of Biological Macromolecules", 1969, pub. Marcel Dekker Inc., New York, pp. 213-290. Glycerol and urea are hereby especially preferred.

As inhibitors, there can also be used chaotropic ions such as thiocyanates and iodides. Examples of other appropriate ions include fluorides, bromides, perchlorates, guanidine and sulphates. Their abstraction for the purpose of removing the precipitation inhibition can take place by extraction with, for example, organic solvents or mixtures of organic solvents, for example esters, or mixtures of organic solvents and water, for example water/alcohol mixtures, possibly with the addition of ionophores or the like. As a rule, it is hereby already sufficient to change the ionic strength in order to achieve the desired effect but a complete removal of the inhibitor can also take place. An addition of a complex former, such as ethylenediamine-tetraacetic acid (EDTA), can also be considered, for example for the removal of inhibiting metal salts, such as magnesium chloride.

The molar concentrations of the immuno-reactive components leading to the precipitation can be varied within wide limits. In the case of the present invention, they are preferably used in such a manner that that component, the immuno-reactivity of which is to be utilised in the finished carrier material, is not present in excess. The component leading to the precipitation is especially preferably used in the ratio of the Heidelberger maximum. This means that the two reaction components are used in the ratio which is most favourable for the precipitation. This ratio can easily be previously ascertained by turbidity tests. An appropriate turbidity curve is to be found, for example, in "Methods in Immunology and Immunochemistry", Volume III, pub. Academic Press, Chapter 13, page 10. In the case of the production of such a curve, the turbidity is plotted which is obtained in the case of constant amount of one of the reaction components with increasing amounts of the other reaction component. The turbidity maximum is the Heidelberger maximum.

In order to achieve maximum stability of the carrier-fixed immuno-reactive body, one of the components of the immuno-precipitation should preferably be a precipitating antibody with an affinity for the antigen which is as high as possible.

The components of the immuno-precipitation in the scope of the present invention are, on the one hand, an antigen, for example a hapten or a protein, and, on the other hand, an antibody. The antigen can, of course, itself also be an antibody. In such a case, i.e. when the immuno-reactive component to be precipitated is itself an antibody, this can also be used as a Fab, Fab' or (Fab')$_2$ fragment, namely, not only of a monoclonal but also of a polyclonal antibody. The precipitating antiantibody which is then used for the precipitation must be correspondingly chosen. The anti-antibody itself can then be polyclonal or monoclonal or a (Fab')$_2$ fragment thereof. If the anti-antibody is a monoclonal antibody or a fragment thereof, then this should preferably recognise two different epitopes on the antigen. However, monoclonal antibodies or (Fab')$_2$ fragments thereof can also be used which only recognise one epitope, which is more usual, if this epitope is present at least twice on the antigen. Mixtures of monoclonal antibodies can also be used as anti-antibody fraction for the immuno-precipitation.

As immuno-reactive material to be precipitated, there can preferably also be used a protein to which a hapten or antigen is coupled. In this case, a precipitating antibody is preferably used as second component of the immune reaction which is directed against the protein. In a further embodiment, a hapten or antigen can be coupled to the precipitating antibody. The other component of the immune reaction can thereby be unlabelled or be coupled with the same or another hapten or antibody. Alternatively, the protein to be precipitated is itself a specific antibody which is precipitated by an anti-antibody.

As already mentioned above, it is a special advantage of the process according to the present invention that at least one component of the immune reaction can be used in non-purified form. In contradistinction to the known immuno-precipitation processes, in which the precipitation takes place immediately after combination of the immune reaction components, in the case of the process according to the present invention, the speed of the precipitation in suspension or in the porous carrier material can take place controlled in such a manner that no entrainment effects occur in the case of foreign substances and the latter do not have to be previously removed but rather can simply be washed out after the immuno-precipitation. Such a washing step is preferred since no precipitate particles, less stable immuno-complexes and adsorptively bound antigens are hereby removed. Therefore, for the washing, there can be used buffers of high ionic strength, detergents, organic solvents and the like, as well as additives stabilising the precipitates, such as carbohydrates and proteins.

If a previous purification of the components of the immune precipitation purification is to be omitted, it is preferable first to mix the particular antigen and the particular antibody in the optimum (Heidelberger) ratio, to wash the precipitate obtained and again to dissolve by the addition of the inhibitor of the immuno-precipitation, preferably by the addition of acid. There is thus obtained a mixture of the components of the immuno-precipitation reaction which can be applied directly to the porous carrier material.

Within the scope of the present invention, it is, of course, also possible previously separately to purify the components of the immuno-reaction in the usual way, via immuno-adsorbers, then to elute with an inhibitor and either to use the eluates directly for the process according to the present invention or first to produce a storage-stable form of the reaction components by lyophilisation. The inhibition of the immuno-precipitation, as well as the slowing down of the precipitation in the carrier material after removal of the inhibiting action can be assisted by physical methods, for example lowering the temperature or increasing the viscosity.

As carriers within the scope of the present invention, there can be used carriers which are conventional for immuno-reactive substances. Such a solid carrier material, which is frequently also referred to as a matrix, can be made, for example, of glass, synthetic resin, paper, porous metal and the like, provided that the carrier material is sufficiently permeated by interconnected, liquid-permeable hollow spaces. Natural, synthetic, organic or inorganic polymers can be used. Furthermore, fibrous, spongy or sintered substances can be used. As carrier materials, there can be used planar, particulate or other three-dimensional porous bodies. However, it is preferred to use planar, porous carriers, such as paper, films of foamed material, glass fibre mats and the like. Since the process according to the present invention gives a completely homogeneous distribution of the immuno-reactive substance in this planar matrix, a dosaging can take place extremely simply on the basis of unit surface areas. Such immuno-reactive, planar carrier materials are especially suitable for use as solid phases in heterogeneous immunoassays.

The use of an immuno-reactive carrier material produced according to the present invention in the scope of a heterogenous enzyme immunoassay can, for example, take place in such a manner that hapten (H) or protein (P), which is contained in a sample, such as buffer solution, serum, plasma, urine culture supernatant or the like, is mixed with a labelled binder (B). As binders, there can be used, inter alia, antibodies, Fab$^-$ fragments or Fab fragments, as well as ligands, which react specifically with the hapten or protein. As labelling for the binder, there can be used, for example, an enzyme, a fluorescent label or radioisotope and, in the following Examples, $\beta$-galactosidase is used. The molar amount of the added binder can be not only in excess but also in insufficiency with regard to the hapten or protein present in the sample.

This mixture is incubated for a constant time during which the complexes H-B or P-B are formed. After the expiry of this period of time, three species are present in the reaction mixture, namely, the complex consisting of hapten/protein, and binder (H-B, P-B), residual free hapten/protein (H/P) and residual free binder (B).

The separation of these species takes place in a second step by means of immunosorption. For this purpose, the mixture is applied to immuno-precipitation solid phase produced according to the present invention which contains bound the hapten to be detected or the antibody to the protein to be determined.

In the case of the hapten test, the free binder but not the binder saturated with hapten binds to the solid phase. Consequently, the supernatant or the eluate of the solid phase contains the binder saturated with the hapten of the sample. The quantitative determination of the hapten now takes place via the labelling of the binder and, in the following Examples, via the determination of $\beta$-galactosidase by means of o-nitrophenyl-$\beta$-D-galactoside or chlorophenol red $\beta$-D-galactoside.

In the case of the protein test, the complex of protein and binder but not the free binder binds to the solid phase, residues of the free binder are removed by washing from the immunosorbent produced according to the present invention. The quantitative detection of the protein takes place via the labelled binder and, in the following Examples, via the determination of the $\beta$-galactosidase by means of o-nitrophenyl-$\beta$-D-galactoside or chlorophenol red $\beta$-D-galactoside.

Another use is in competitive immuno-tests. The use of the immuno-reactive carrier material produced according to the present invention can take place in such a manner that the analyte (hapten or protein), which is contained in the sample, is mixed with a constant amount of labelled analyte. The labelling can be, for example, an enzyme, a fluorescent label, radioisotope or the like. This mixture is applied to the matrix. On the matrix, there is immobilised an antibody which is directed against the analytes. The mixture is incubated on the matrix for a definite time. During this time, not only unchanged analyte but also labelled analyte compete for the binding places on the matrix. The more analyte is present in the sample, the less labelled analyte is bound by the matrix and vice versa. At the end of the incubation phase, the liquid is removed from the porous matrix, for example by centrifuging. The amount of labelled analyte is then determined either in the free phase or bound to the matrix.

Another use of the carrier material produced according to the present invention can take place in such a manner that the analyte (hapten or protein) is mixed with a constant amount of labelled antibody which is directed against the analyte. Possible kinds of labelling of the antibody have been described hereinbefore. This mixture is then either incubated for a definite time and then applied to the porous carrier material or, alternatively, applied to the porous carrier material immediately after mixing. If the analyte is a hapten, the carrier material contains the hapten to be detected or a derivative thereof in fixed form and if the analyte is a protein, the carrier material contains the protein to be detected or a derivative thereof also in fixed form. If the first mixture is incubated before application to the carrier material, then labelled antibody binds with remaining free binding places to the porous carrier material. If the mixture is applied immediately to the carrier material, then the analyte from the sample and the analyte fixed on the carrier material compete for the binding places of the labelled antibody. At the end of the incubation phase, the liquid is removed from the porous carrier material and the amount of labelled antibody is determined either in the liquid phase or on the porous carrier material.

Figure 1:
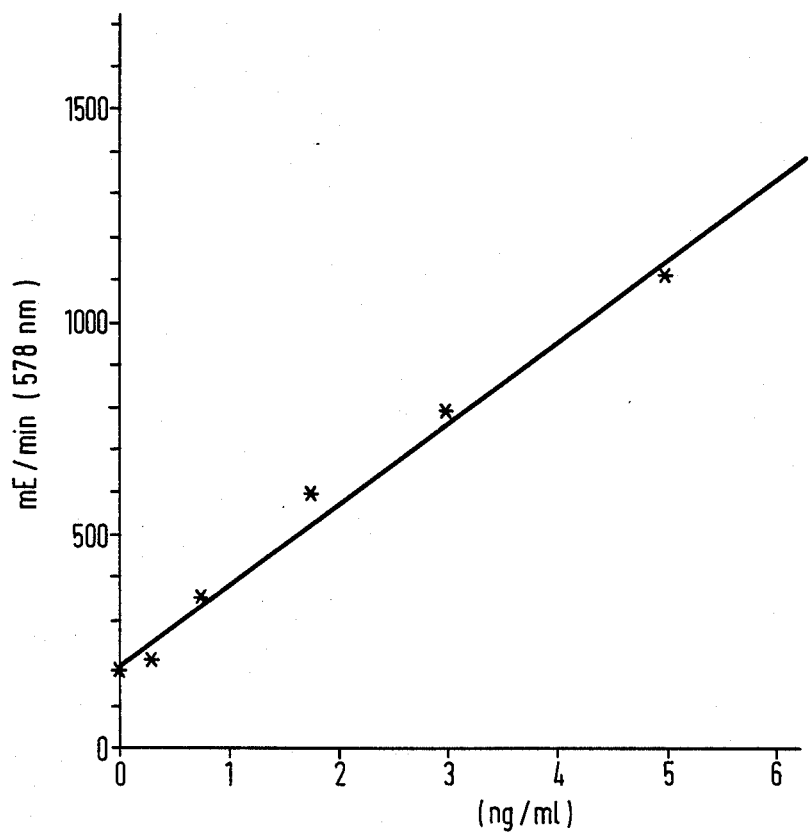
FIG. 1 is a calibration curve obtained with the digoxin immune precipitation fleece of example 3.

The following Examples are given for the purpose of illustrating the present invention.

Obtaining the materials used for the tests and carrying out of the test:

(a) Production of polyhaptens (PH)

The production of PH is known in the art. Thus, for examle, a digoxin PH or a diphenylhydantoin PH can be obtained via reactive asymmetrical dicarboxylic acid ester/activated hapten ester and binding thereof to a carrier protein.

The preparation of T3- or T4-PH can take place, for example, by direct coupling of the $NH_2$ groups of hormone and protein by means of bis-imidates (see European Patent Specification A 0078952) or by the carbodiimide reaction (see Aherne et al., *Brit. J. Clin. Pharm.*, 3, 56/1976) or by the mixed anhydride reaction (see Erlanger et al., Methods in Immunology and Immunochemistry, ed. Williams and Chase, pub. Academic Press, New York, 1967, pp. 149 et seq.). Alternatively, in a first step, the $NH_2$ function of T3 or T4 can be protected with an acetyl, trifluoroacetyl, tert.-butoxycarbonyl or benzyloxycarbonyl group. Subsequently, the carboxyl function is converted into an activated ester, for example N-hydroxysuccinimide ester, N-hydroxyphthalimide ester, N-hydroxybenztriazole ester. An example of such an activated T4 is described in Example 3 of European Patent Specification A 0108400. Reaction with the carrier protein gives the PH.

The choice of the carrier proteins is not subjected to any limitations insofar as a corresponding "precipitating" antibody is available or can be produced.

Insofar as a immunosorptive purification of antigen and antibody has taken place, as carrier there was used the "affinity adsorber, glutardialdehyde activated" of Boehringer Mannheim GmbH (order No. 665525). For the Examples described hereinafter, according to the instructions of the manufacturer, for the antigen purification a sheep antibody against rabbit IgG or a specific antibody against the hapten was bound to the carrier and for the antibody purification rabbit IgG was bound to the carrier. The immunosorption took place as described in the working instructions for the affinity absorbent.

(b) Production of the binder (digoxin as example)

Obtaining the antiserum directed against digoxin

The production of the immunogen, namely, human serum albumin conjugated with digoxin, took place in the manner described in detail by V. P. Butler jr. and J. P. Chen., Proc. Nat. Acad. Sci, US., 51, 71–78/1967, as well as by T. W. Smith, V. P. Butler and E. Haber, Biochemistry, 9, 331–337/1970. Sheep were immunised with this immunogen and the corresponding antiserum obtained.

Production of the binder

Antiserum directed against digoxin was purified to the IgG fraction via ammonium sulphate precipitation and passage over DEAE-cellulose. Papain splitting was carried out according to the method of R. R. Porter (Biochem. J., 73, 119–126/1959).

The Fab fragments were separated off from the non-digested IgG molecules and the Fc fragments by means of gel filtration over Sephadex G 100 and ion exchanger chromatography over DEAE-cellulose according to the methods described in the literature (see K. Malinowski and W. Manski in "Methods in Enzymology"; J. J. Langone and H. van Vunakis eds., pub. Academic Press, Vol. 73, 418–459/1981). The resulting Fab fraction was purified chromatographically and coupled to β-galactosidase according to the method of T. Kitiwaga in "Enzyme Immunoassay", Ishikawa. T. Kawai and K. Miyai eds., Igaku Shoin, Tokyo-New York, pp. 81–89/1981.

(c) Production of sheep antibody against rabbit or mouse IgG/Fcγ

Rabbit slaughter serum or mouse serum was subjected to an ammonium sulphate precipitation. After passage over DEAE-cellulose and papain splitting, gel and ion exchange chromatography (see (b)), there are obtained the Fc fragments of the rabbit and mouse IgG's as immunogens.

The working up of the sheep antisera took place as described under (b) (immunosorption see (a)).

(d) Carrying out of the test (digoxin as example)

Digoxin standards in human serum (taken from the ELISA kit of Boehringer Mannheim GmbH; order No. 199656) were diluted 1:7.5 with 0.9% aqueous sodium chloride solution. 200 μl. diluted standard and 200 μl. binder (20 mU/ml., determined with o-nitrophenyl-β-D-galactoside), produced as described in (b), were incubated in phosphate-buffered saline (PBS)(pH 7.2) at 37° C.

Thereafter, 50 μl. of the mixture were applied to 1 cm² of the planar, immuno-reactive carrier material. Incubation is carried out for a further 5 minutes at 37° C., followed by centrifugation for 1 minute in an Eppendorf centrifuge.

The enzyme activity of the digoxin-binder complex can now be determined in the free phase kinetically by the addition of chlorophenol red β-D-galactoside (prepared according to Federal Republic of Germany Patent Specification No. 33 45 748) and measured at 578 nm.

In the Examples, there is, in each case, shown the course of the "rising" calibration curve, the digoxin concentration of the undiluted serum (X axis) being plotted against the measured optical density at 578 nm (Y axis).

Alternatively, the excess amount of binder, i.e. the amount bound to the solid phase, can be determined as above and plotted against the particular digoxin concentration, a "decreasing" calibration curve being obtained.

EXAMPLE 1

Preparation of T3 (triiodothyronine) immune precipitate fleece

As antigen, there was used polyhapten consisting of rabbit IgG and T3 bound thereto (mole ratio IgG:T3=1:3). The antigen was purified immunosorptively over an anti-T3 column (see (a)).

As antibody, there was used polyclonal antibody directed against the Fc part of the rabbit IgG. The antibody was purified immunosorptively over a rabbit IgG column (see (a)).

As fleece, there was used a mixed fleece of cellulose and polyester (obtained from Kalff, Euskirchen, Germany) or of lint, cellulose and polyamide (obtained from Binzer, Hatzfeld, Eder, Germany).

Antigen and antibody were taken up separately in 1 mM acetic acid (in each case $c = 1$ mg./ml.) and left to stand for 1 hour at ambient temperature. The solutions were then mixed in a ratio of 1:3 (the antigen/antibody ratio that corresponded to the Heidelberger maximum) and diluted with a ninefold volume of a solution of 250 mM acetic acid and 5 mM sodium acetate.

The fleece was drawn through the impregnation solution, squeezed out and dried for 60 minutes at 30° C. in a circulating-air drying cabinet. It was then washed by descending chromatography for 1 hour with PBS buffer (pH 6.0) and dried for 30 minutes at 30° C. in a circulating air drying cabinet.

The ratio of measurement range (standard 5 ng. T3/ml.-standard 0) to standard 0 was 11.8 (see Table 1).

TABLE 1

Comparison of T3 immune precitate fleece prepared by different processes

| process | Example | measurement range/standard 0 |
| --- | --- | --- |
| hom. 2-step | 2 | 12.0 |
| hom. 1-step | 1 | 11.8 |
| heterog. 2-step | analogue 4 | 1.6 |
| suspension | analogue 5 | 0.19 |

EXAMPLE 2

Preparation of T3 immune precipitate fleece (homogeneous 2-step process)

Antigen, antibody and fleece are the same as in Example 1. The fleece is impregnated with 50 mM aqueous sodium chloride solution and subsequently dried for 30 minutes at 50° C. in a circulating-air drying cabinet.

Antigen and antibody are taken up separately in 1 mM acetic acid (in each case $c = 1$ mg./ml.) and left to stand for 1 hour at ambient temperature. The two solutions are mixed in a ratio of 1:3 and diluted with a ninefold volume of 50 mM acetic acid.

The solution is applied to the fleece (liquid saturation of the fleece) and the impregnated fleece is dried for 60 minutes at 30° C., in a circulating-air drying cabinet. It is then washed by descending chromatography with PBS buffer (pH 6.0) and dried for 30 minutes at 30° C. in a circulating-air drying cabinet.

The ratio of measurement range (standard 5 ng. T3/ml.-standard 0) to standard 0 in 12.0 (see Table 1).

EXAMPLE 3

Preparation of digoxin immune precipitate fleeces (homogeneous 1-step process)

As antigen, there was used polyhapten, consisting of rabbit IgG and digoxin bound thereon (IgG:digoxin 1:3 to 1:4). The antigen was purified immunosorptively via an anti-R-Fc$\gamma$ column (see (a)).

As antibody there was used the same polyclonal antibody as in Example 1.

As fleece, there was used a mixed fleece of cellulose and polyester (obtained from Kalff, Euskirchen, Germany).

Antigen and antibody were taken up separately in 100 mM acetic acid is concentrations of 1 mg./ml. and 3.5 mg./ml., respectively, and the two solutions mixed in a ratio of 1:1. The impregnation solution was then diluted with the four-fold volume of 200 mM sodium citrate buffer (pH 3.0).

The fleece was drawn through the impregnation solution, squeezed out, dried for 10 minutes at 75° C. with circulating air and subsequently washed as in Example 1 and dried as before.

The calibration curve shown in FIG. 1 of the accompanying drawings was obtained with the so-produced digoxin immune precipitate fleeces. The standards 0, 0.3, 0.75, 1.75, 3 and 5 ng. digoxin/ml. were used. The ratio of measurement range (standard 5 ng. digoxin/ml.-standard 0) was 4.9.

EXAMPLE 3a

Preparation of digoxin immune precipitate fleece (without washing step)

Antigen (200 mg./l.) and antibody (700 mg./l.) are taken up separately in 50 mM acetic acid. After 15 to 30 minutes at ambient temperature, the two solutions are mixed in the ratio of 1:1. In a subsequent step, this solution is diluted with the same volume of 50 mM acetic acid plus 40 mM sodium chloride. Fleece are impregnated therewith and then dried for 10 minutes at 75° C.

The fleece is used directly in the test. The calibration curve obtained therewith corresponds to FIG. 1 of the accompanying drawings.

EXAMPLE 4 (comparison)

Preparation of digoxin immune precipitate fleece (heterogenous 2-step process)

Antigen, antibody and fleece are the same as in Example 3.

Antigen and antibody are taken up separately in 1 mM acetic acid ($c = 5$ mg./ml. and 17.5 mg./ml., respectively). They are left to stand for 30 minutes at ambient temperature, then the antigen solution is diluted with a 50 fold volume of PBS buffer (pH 6.0) and impregnated on to the fleece which is dried for 10 minutes at 75° C. in a circulating-air drying cabinet. The dried fleece is subsequently impregnated with the antibody solution which have been diluted 50 fold with the above buffer, followed by drying for 10 minutes at 75° C. After washing the fleece with the same buffer, it is dried for 10 minutes at 75° C.

Figure 2:
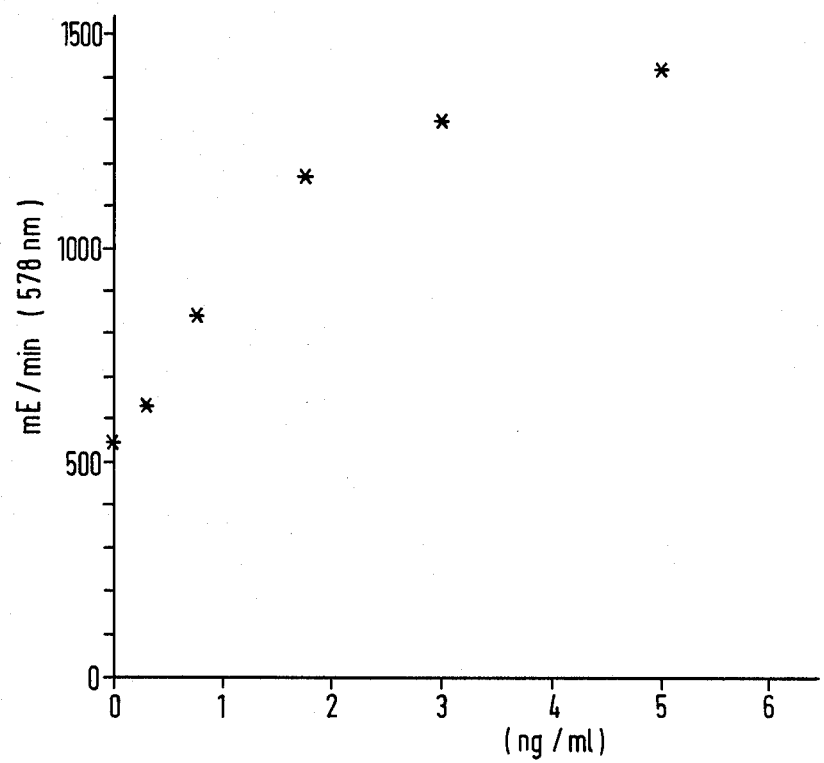
FIG. 2 is a calibration curve obtained with the digoxin immune precipitation fleece of example 4.

The curve obtained from the calibration graph is shown in FIG. 2 of the accompanying drawings. The ratio of measurement range (standard 5 ng. digoxin/ml.-standard 0) to standard 0 is 1.6.

As an alternative to the above procedure, the antibody can be impregnated first of all, followed by the antigen.

EXAMPLE 5 (comparison)

Preparation of digoxin immune precipitate fleece (suspension process)

Antigen, antibody and fleece are the same as in Example 3. Antigen and antibody are each taken up in 100 mM acetic acid (c=1 mg./ml. and 3.5 mg./ml., respectively) and left to stand for 15 minutes at ambient temperature. 1 part of the antigen solution, 1 part of the antibody solution and 1.5 parts of 100 mM potassium phosphate buffer (pH 7.6) are mixed and then left to stand for 1 hour at ambient temperature. The suspension formed is centrifuged off, the supernatant is discarded and the precipitate is resuspended (homogenised) in a 9 fold volume of PBS buffer (pH 6.0). The suspension is impregnated on to the fleece in such a manner that the fleece is saturated with liquid. Thereafter, the fleece is dried for 10 minutes at 75° C. in a circulating-air drying cabinet. After washing for 1 hour with PBS buffer (pH 6.0), the fleece is again dried for 10 minutes at 75° C.

Figure 3:
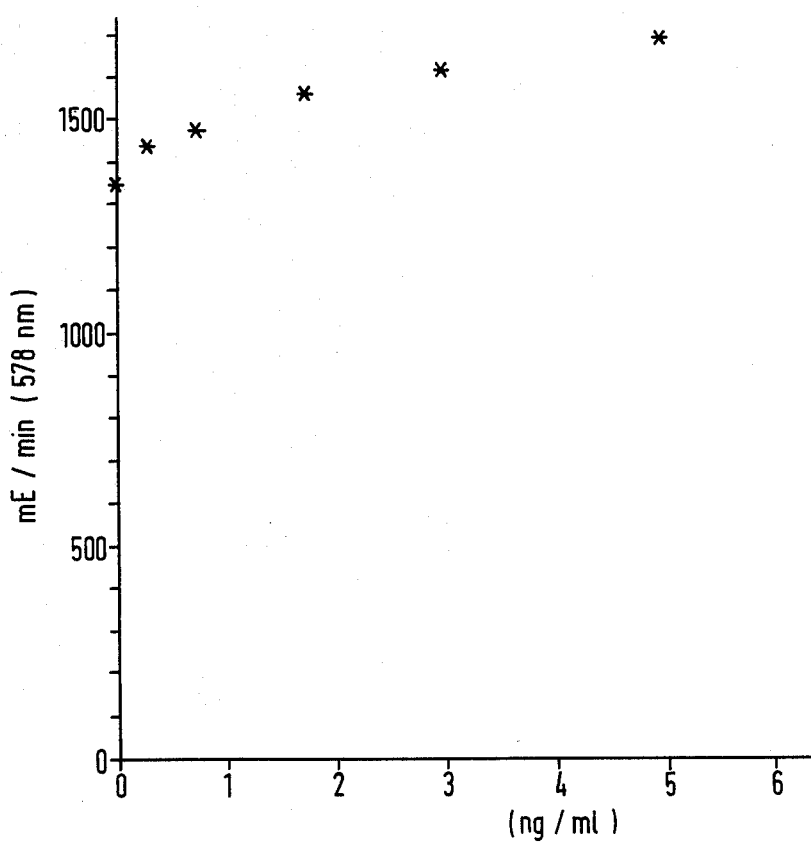
FIG. 3 is a calibration curve obtained with the digoxin immune precipitation fleece of example 5.

The curve obtained from the calibration graph is shown in FIG. 3 of the accompanying drawings. The ratio of measurement range (standard 5 ng. digoxin/ml.-standard 0) to standard 0 is 0.19.

EXAMPLE 6

Preparation of diphenylhydantoin (DPH) immune precipitate fleece (homogeneous 1-step process with precipitate washings)

As antigen, there was used polyhapten consisting of rabbit IgG and diphenylhydantoin bound thereon.

As antibody, there was used polyclonal antibody directed against the Fc part of the rabbit IgG.

As fleece, there was used a mixed fleece of cellulose and polyester (obtained from Kalff, Euskirchen, Germany).

Antigen and antibody (each purified non-immunosorptively) are each taken up in 100 mM acetic acid (c=1 mg./ml. and 20 mg./ml., respectively) and left to stand for 15 minutes at ambient temperature.

1 part of antigen solution, 2 parts of antibody solution and 2 parts of 100 mM potassium phosphate buffer (pH 7.6) are mixed and the suspension left to stand for 1 hour at ambient temperature. The precipitate is centrifuged down the supernatant is discarded and the precipitate is resuspended in a ninefold volume of 100 mM potassium phosphate buffer. This centrifugation/washing step is repeated three times and then the precipitate is washed twice in the same manner with distilled water to remove the salt.

The precipitate is taken up in 100 mM acetic acid (c=5 mg./ml.). The clear antigen/antibody solution is left to standard for 15 minutes at ambient temperature and then diluted with a fivefold volume of 200 mM sodium citrate buffer (pH 3.0).

The fleece is drawn through this impregnation solution, squeezed out, dried for 10 minutes at 75° C. and subsequently washed as in Example 1 and dried as before.

Figure 4:
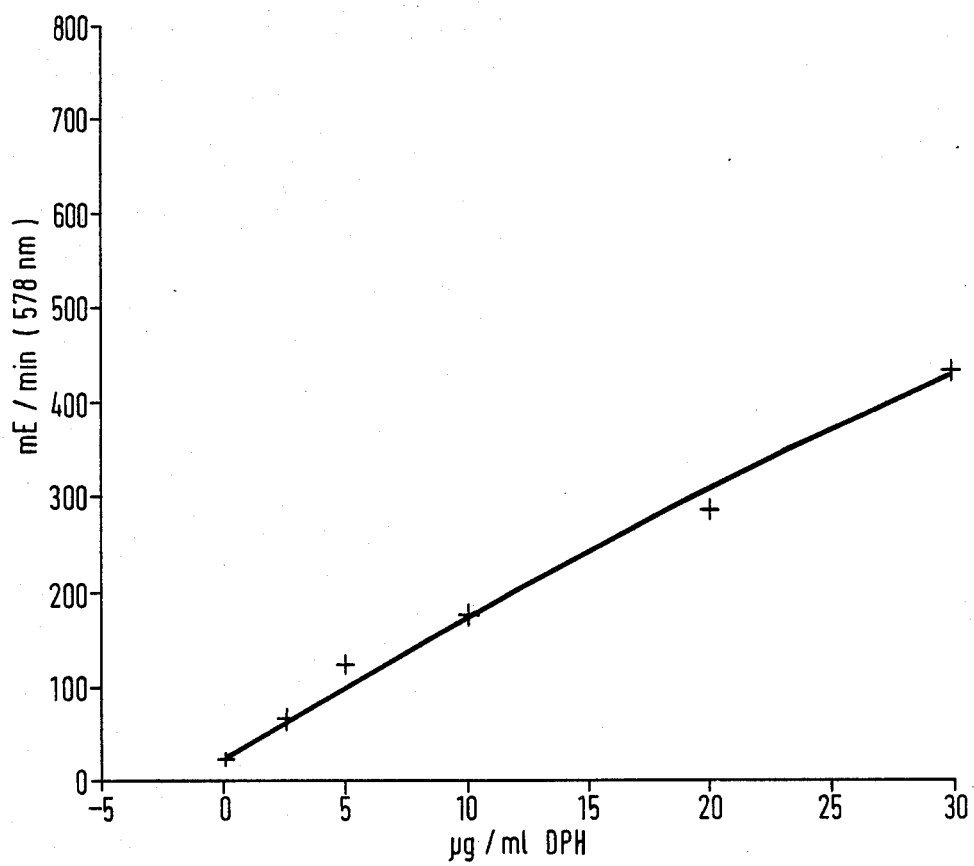
FIG. 4 is a calibration curve obtained with the DPH immune precipitate fleece of example 6.

The calibration curve shown in FIG. 4 of the accompanying drawings is obtained with the so-produced DPH immune precipitate fleece. The standards 0. 2.5, 5, 10, 20 and 30 μg. DPH/ml. are used. The ratio of measurement range (standard 30 μg. DPH/ml.-standard 0) to standard 0 is 18.2.

EXAMPLE 7

Preparation of TSH immune precipitate fleece (homogeneous 1-step process with precipitate washing)

As antigen there was used monoclonal antibody directed against human TSH. The antibody (from ascites) was purified by ammonium sulphate precipitation and chromatography on DEAE-cellulose.

As antibody there was used polyclonal antibody directed against the Fc part of mouse IgG. The antibody was purified by ammonium sulphate precipitation and chromatography on DEAE-cellulose.

As fleece there was used a mixed fleece of cellulose and polyester (obtained from Kalff, Euskirchen, Germany).

Antigen and antibody were each taken up in 100 mM potassium phosphate buffer (pH 6.0) and 0.9% sodium chloride (c=1 mg./ml. and 17 mg./ml., respectively). The two solutions were mixed and the suspension then left to stand for 30 minutes at ambient temperature. The precipitate was centrifuged down, the supernatant was discarded and the precipitate was resuspended in a ninefold volume of the above buffer. This centrifugation/washing procedure was repeated five times and then the precipitate was washed twice in the same manner with distilled water to remove the salt.

The precipitate was taken up in 50 mM acetic acid (c=5 mg./ml.), the clear antigen/antibody solution then left to stand for 15 minutes at ambient temperature and subsequently diluted with fourfold volume of 20 mM sodium acetate solution.

The fleece is drawn through this impregnation solution, squeezed out and then dried for 30 minutes at 37° C. in a circulating-air drying cabinet. It is then washed for 1 hour by descending chromatography with phosphate buffer (pH 6.5) and dried for 30 minutes at 37° C.

Figure 5:
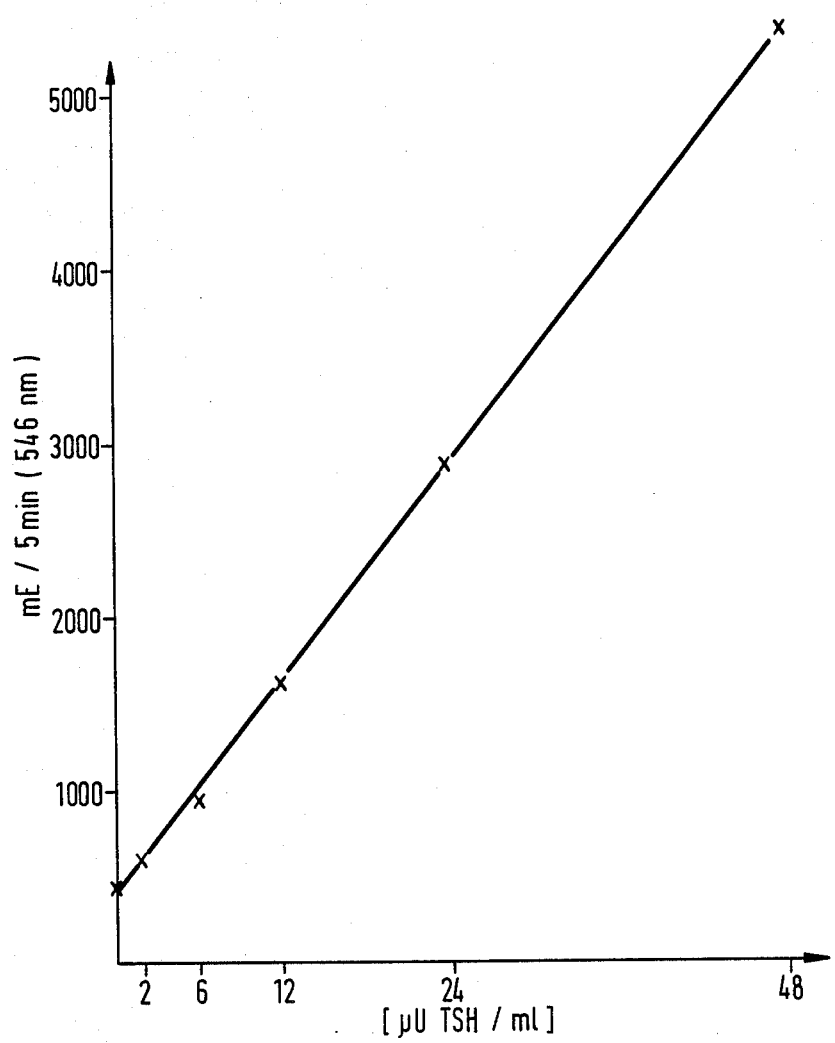
FIG. 5 is a calibration curve obtained with the TSH immune precipitate fleece of example 7.

The calibration curve shown in FIG. 5 of the accompanying drawings was obtained with the so-produced TSH immune precipitate fleece. The standards 0, 2, 6, 12, 24 and 48 μU TSH/ml. were used.

EXAMPLE 8

Preparation of TSH immune precipitate fleece (homogeneous 2-step process with precipitate washing)

The washed precipitate of Example 7 was used. Use was also made of the same fleece as in Example 7. The dried fleece was subsequently impregnated with 50 mM aqueous sodium chloride solution and dried for 10 minutes at 75° C.

The precipitate was taken up in an amount of 500 mM acetic acid which was just sufficient to dissolve the precipitate. It was then diluted with 5 mM acetic acid to c=1 mg./ml. The solution was applied to the fleece in an amount sufficient to saturate the fleece with the liquid. The fleece was then dried for 30 minutes at 30° C. in a circulating air drying cabinet. The fleece was then washed chromatographically with sodium acetate solution and subsequently with phosphate buffer (pH 6.5) and dried at 37° C.

Figure 6:
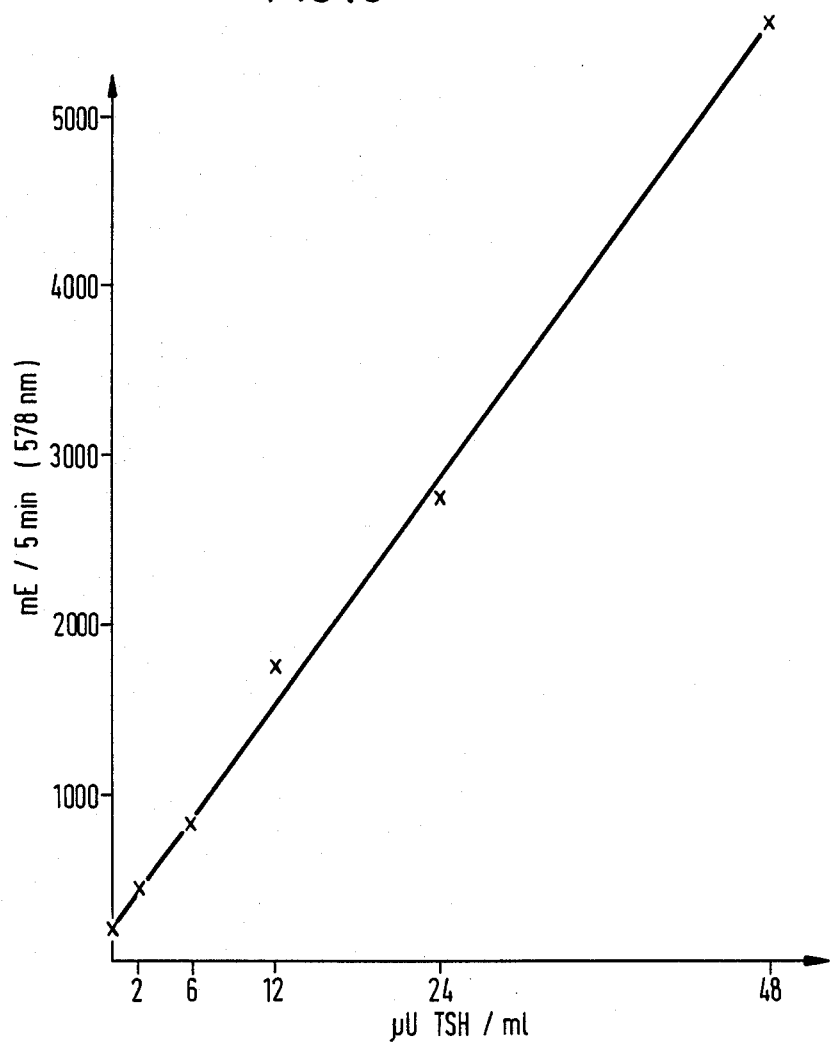
FIG. 6 is a calibration curve obtained with the TSH immune precipitate fleece of example 8.

The calibration curve shown in FIG. 6 of the accompanying drawings was obtained with the so-produced TSH immune precipitate fleece. The standards 0, 2, 6 12, 24 and 48 IU TSH/ml. were used.

EXAMPLE 9

Comparison of the stabilities of the impregnation solutions

Figure 7:
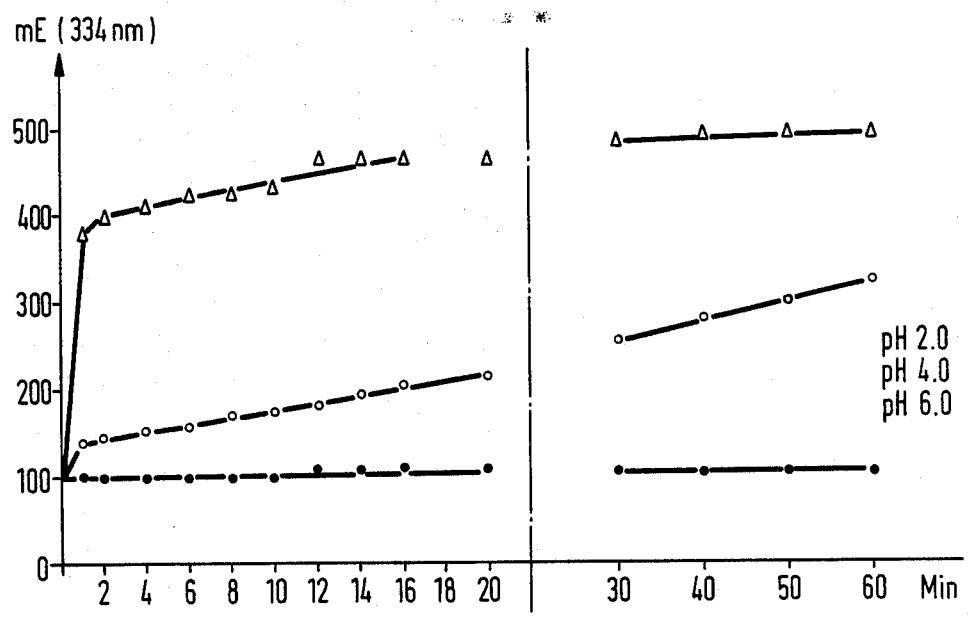
FIG. 7 shows the effect of pH on solution stabilities (precipitation formation versus time).

Antigen and antibody are the same as in Example 1. Antigen and antibody are, in each case, separately dissolved in a solution of inhibitor, 0.1M aqueous sodium chloride solution and 0.5% bovine serum albumin. The two solutions are adjusted with 0.2N hydrochloric acid (acetic acid and propionic acid give comparable results) to pH 6.0, pH 4.0 and pH 2.0. The solutions of antigen and antibody of the same pH are then mixed and the chronological course of the precipitate formation is monitored. FIG. 7 of the accompanying drawings shows that at pH 6.0, immediately after mixing of antigen and antibody, immuno-precipitation takes place. At pH 4.0 there is a poorer precipitation which is not completed after 1 hour and at pH 2.0 precipitation no longer occurs.

EXAMPLE 10

Preparation of T4 tetraiodothyronine immune precipitate fleece (without washing step)

As antigen there was used polyhapten consisting of rabbit IgG and T4 bound thereon (mole ratio of IgG:T4=1:3). The antigen was purified immunosorptively over an anti-T4 column (see (a)).

As antibody there was used polyclonal antibody directed against the Fc part of the rabbit IgG. The antibody was purified immunosorptively over a rabbit IgG column (see (a)).

As fleece there was used a mixture of cellulose and polyester (obtainable from Kalff, Euskirchen, Germany) or of lint, cellulose, polyamide (obtainable from Binzer, Hetzfeld, Eder, Germany).

Preparation of the matrix

Antigen (400 mg/l) and antibody (1400 mg/l) were taken up separately in 50 mM acetic acid plus 0.5% sodium chloride. After 15 to 30 minutes, both solutions were mixed in a ratio of 1/1 and fleece impregnated therewith. After drying for 10 minutes at 75° C., the fleece was impregnated with PBS and dried for 10 minutes at 75° C.

EXAMPLE 10a

Preparation of T4 immune precipitate fleece (with washing step)

Antigen (2 mg./ml.) and antibody (7 mg./ml.) are dissolved separately in distilled water. Both solutions are diluted with 50 mM aqueous trisodium phosphate solution in the ratio of 1+4. Equal volumes of the diluted solutions are mixed and fleece impregnated therewith. The fleece are dried for 10 minutes at 75° C. in a circulating-air drying cabinet. Subsequently, the fleece are washed by descending chromatography with 10 mM phosphate buffer, until the eluate has a pH value of 5.0. After washing, the fleece are dried.

EXAMPLE 10b

Preparation of T4 immune precipitate fleece (without washing step)

Antigen (2 mg./ml.) and antibody (7 mg./ml.) are dissolved separately in distilled water. Both solutions are diluted with 50 mM aqueous ammonia solution in the ratio of 1+4. Equal volumes of the diluted solutions are mixed and fleece impregnated therewith. The fleece are dried for 10 minutes at 75° C. and used directly in the test.

The calibration curves obtained with the fleece of Examples 10, 10a and 10b correspond to the calibration curves of the preceding Examples.

We claim:

1. In a process for the preparation of a porous carrier material containing an immuno-reactive first component by application to said carrier material of a solution of said first component and a solution of a second component which immuno-precipitates said first component without perturbing the immuno-reactivity of said first component, and subsequent drying of the carrier material impregnated with said immuno-precipitated first component, wherein the improvement comprises the steps of impregnating said carrier material with a solution of said first and second components plus an inhibitor of the immuno-precipitation reaction, and initiating said immuno-precipitation by removal of said inhibitor or by neutralization of its inhibiting action.

2. Process according to claim 1, wherein the components of the immuno-precipitation reaction are a protein and an antibody or a fragment thereof directed against this protein.

3. Process according to claim 2, wherein a protein is used to which a hapten or antigen is coupled.

4. Process according to claim 2, wherein one of said components is an antibody or a fragment thereof directed against the protein to which antibody or fragment thereof is coupled a hapten or antigen.

5. Process according to claim 2, wherein a specific antibody is used as protein.

6. Process according to claim 1 wherein the inhibitor is an acid or a base.

7. Process according to claim 4, wherein the inhibitor is a volatile acid or base and the removal of the inhibitor is by evaporation.

8. Process according to claim 6, wherein the inhibitor is is a non-volatile acid or base and a carrier material is employed which is impregnated with a salt of a volatile acid or base.

9. Process according to claim 1 wherein the inhibitor is glycerol or urea and, after impregnation of the carrier material, the inhibitor is removed by extraction with a mixture of at least one organic solvent and water.

10. Process according to claim 1 wherein the inhibitor is a metal salt, the inhibiting action of which in the carrier material is neutralized by means of a complex former.

11. Process according to claim 1 wherein the inhibitor is a chaotropic ion of the Hofmeister series.

12. Process according to claim 11, wherein the inhibitor is a thiocyanate.

13. Process according to claim 11, wherein the inhibitor is an alkali metal iodide.

14. Process according to claim 1 wherein the first and second components of the immuno-precipitation reaction are used in the ratio of the Heidelberger maximum.

15. Process according to claim 1 wherein at least one component of the immuno-precipitation reaction is used in non-purified form.

16. Process according to claim 1 wherein the solution of both components of the immuno-precipitation reaction is first prepared as a suspension precipitate which, after washing, is dissolved by the addition of an inhibitor and subsequently used for the impregnation of the porous carrier.

17. The process of claim 11, wherein the improvement comprises the further step of washing said carrier material containing immuno-precipitated first component.

* * * * *

UNITED STATES PATENT AND TRADEMARK OFFICE
CERTIFICATE OF CORRECTION

PATENT NO. : 4,820,644

DATED : April 11, 1989

INVENTOR(S) : Rainer Schafer, et al.

It is certified that error appears in the above-identified patent and that said Letters Patent is hereby corrected as shown below:

Col. 14, line 45 -
    Claim 7, line 1:    after "claim" delete "4" and insert -- 6 --.

Col. 16, line 3 -
    Claim 17, line 1:    after "claim" delete "11" and insert -- 1 --.

Signed and Sealed this

Fifth Day of December, 1989

Attest:

JEFFREY M. SAMUELS

*Attesting Officer*    *Acting Commissioner of Patents and Trademarks*

UNITED STATES PATENT AND TRADEMARK OFFICE
CERTIFICATE OF CORRECTION

PATENT NO. : 4,820,644

DATED : April 11, 1989

INVENTOR(S) : Rainer Schafer et al.

It is certified that error appears in the above-identified patent and that said Letters Patent is hereby corrected as shown below:

Title Page, Inventors:

add: --Dieter Mangold of Mannheim, Fed. Rep. of Germany--

Signed and Sealed this

Twenty-third Day of January, 1990

Attest:

JEFFREY M. SAMUELS

Attesting Officer    Acting Commissioner of Patents and Trademarks